United States Patent [19]

Van Alstine

[11] Patent Number: 5,108,568
[45] Date of Patent: Apr. 28, 1992

[54] CONTROLLED METHOD OF REDUCING ELECTROPHORETIC MOBILITY OF MACROMOLECULES, PARTICLES OR CELLS

[75] Inventor: James M. Van Alstine, Huntsville, Ala.

[73] Assignee: The United States of America as represented by the Administrator of the National Aeronautics and Space Administration, Washington, D.C.

[21] Appl. No.: 599,601

[22] Filed: Oct. 18, 1990

Related U.S. Application Data

[63] Continuation-in-part of Ser. No. 376,487, Jul. 7, 1989.

[51] Int. Cl.$^5$ .............................................. G01N 27/26
[52] U.S. Cl. .............................. 204/180.1; 204/183.3; 204/299 R
[58] Field of Search .............. 204/180.1, 183.3, 299 R

[56] References Cited

U.S. PATENT DOCUMENTS

| | | | |
|---|---|---|---|
| 3,984,533 | 10/1976 | Uzgiris | 204/299 R X |
| 4,011,044 | 3/1977 | Uzgiris | 204/183.3 X |
| 4,102,990 | 8/1978 | Uzgiris | 204/299 R X |
| 4,181,589 | 1/1980 | Brooks | 204/180.1 |
| 4,783,419 | 11/1988 | Hayashi et al. | 204/183.3 X |

OTHER PUBLICATIONS

Müller, W. et al., "Polyethylene Glycol Derivatives of Base and Sequence Specific DNA Ligands: DNA Interaction and Application for Base Specific Separation of DNA Fragments by Gel Electrophoresis", Nucleic Acids Research, vol. 9, No. 1, (1981), pp. 95–119.

Primary Examiner—John Niebling
Assistant Examiner—John S. Starsiak, Jr.
Attorney, Agent, or Firm—Robert L. Broad, Jr.; Jerry L. Seemann; John R. Manning

[57] ABSTRACT

A method of reducing electrophoretic mobility of macromolecules, particles, cells and other substances is provided which comprises interacting in a conventional electrophoretic separating procedure the substances with a polymer-linked affinity compound comprised of a hydrophilic neutral polymer such as polyethylene glycol bound to a second component such as a hydrophobic compound, an immunocompound such as an antibody or antibody active fragment, or a ligand such as a hormone, drug, antigen or a hapten. The reduction of electrophoretic mobility achieved is directly proportional to the concentration of the polymer-linked affinity compound employed, and such reduction can comprise up to 100% for particular particles and cells. The present invention is advantageous in that electrophoretic separation can now be achieved for substances whose native surface charge structure had prevented them from being separated by normal electrophoretic means. Depending on the affinity component utilized, separation can be achieved on the basis of specific/irreversible, specific/reversible, semi-specific/reversible, relatively nonspecific/reversible, or relatively nonspecific/irreversible ligand-substance interactions.

10 Claims, 2 Drawing Sheets

CONTROLLED METHOD OF REDUCING ELECTROPHORETIC MOBILITY OF MACROMOLECULES, PARTICLES OR CELLS

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 43 U.S.C. 2457).

This application is a continuation-in-part of U.S. patent application Ser. No. 07/376,487, filed Jul. 7, 1989.

FIELD OF THE INVENTION

The invention relates in general to a method for quantitatively reducing electrophoretic mobility of macromolecules, particles and cells or other substances, and in particular to a method of reducing electrophoretic mobility in a concentration-dependent manner by interacting these substances with a polymer-linked affinity compound comprising a hydrophilic neutral polymer bound to a second component such as a hydrophobic compound, an immunocompound, or a ligand.

BACKGROUND OF THE INVENTION

For years, electrophoresis has been used to separate and isolate macromolecules and particles due to differences in apparent surface charge. When two substances have the same charge but different mobilities, the faster moving substances will overrun and migrate ahead of the slower one. This is usually due to substance geometry and other hydrodynamic considerations, e.g., macromolecular group conformation/surface topography, etc. In general, the affinity of one substance for another will affect the mobility of that substance when both are subjected to electrophoresis. It is thus theoretically possible to maximize separation of particles with the same or similar charge through the use of specific affinity compounds. For a general review of affinity electrophoresis (of macromolecules), see Takeo, *Electrophoresis* 5:187-195 (1984).

Affinity electrophoresis techniques are of enormous potential value in a variety of medical biochemical areas (e.g., research, diagnostics). Of particular importance are techniques for isolating or separating very large molecules or cells such as cancer cells, blood cells, DNA molecules, lymphocytes, proteins, etc. New techniques are needed since in a great number of cases, the cells or particles of interest are not amenable to presently known electrophoretic separation techniques. This is particularly true for cells which are easily damaged by the extreme conditions such as temperature, pH, salt concentration or fluid shear inherent in various electrophoretic techniques. It is also true that most biological cells have reasonably similar electrophoretic mobilities (approximately 0.9 $\pm 0.3$ $\mu ms^{-1}V^{-1}cm$), making them hard to separate electrophoretically. Electrophoretic particle separation and analysis systems need to be specific for various types of particles and cells. It is extremely important that the range of electrophoretic mobility be entirely controlled such as by the addition of compounds which vary mobility in a specific manner, and, preferably in a concentration-dependent manner.

The use of affinity agents such as antibodies to enhance the specificity of electrophoresis and develop a useful system by which a large number of particles and cells could be separated was theorized as early as the 1920's. However, antibody-induced cell aggregation, and a demonstrated lack of cell-antibody interaction appreciably altering substance electrophoretic mobility has kept this goal at arms length. Previous research in this field attempted to use immuno-compounds and other agents to affect electrophoretic mobility of various cells. For example, Seaman, pgs. 1135-1229 in *The Red Blood Cell, Vol.* 3 (1975), discloses modifying red blood cell (erythrocyte) surfaces with such materials as antisera, enzymes, and neutral polymers. In the first two cases (antisera and enzymes), problems were reported including aggregation, limited reduction of cell mobility, and a general lack of specificity in the treatments. It was found that the use of freely absorbed neutral polymers actually increased particle electrophoretic mobility. Effects of unmodified antibodies on red blood cells (such as indicated above) has also been reported by Sachtleben, in *Cell Electrophoresis*, pgs. 100-114 (1965). The use of a double antibody system yielding up to about a 40% reduction in electrophoretic mobility in epithelial cells and lymphocytes was reported in Cohly et al in *Cell Electrophoresis*, pgs. 611-616 (1985). In an attempt to alter net cell surface charge, rather than cell surface electrohydrodynamics, these authors exposed cells covered with antibodies to secondary anti-antibodies possessing a net positive charge which they hoped would partially neutralize the cells native net negative charge (due primarily to surface carboxylate groups). These previous attempts in reducing mobility generally suffered from various problems such as aggregation, and large, controlled reductions in electrophoretic mobility have not been achieved.

In the patent art, many attempts at separating biological cells and other compounds through electrophoresis are known. For instance, U.S. Pat. No. 4,474,886 (Willard) relates to the use of SDS polyacrylamide gel in gel electrophoresis wherein the SDS gel binds to proteins to aid in separation by mass. The SDS is charged and uniformly coats the macromolecule creating uniform charge per unit area. Thus separation is on the basis of surface area which is related to size. SDS kills cells, which regardless cannot be subjected to such gel electrophoresis. Independent of these blocks, this method would not aid in separating two molecular samples of similar mass which have different charges.

As indicated above, the use of neutral polymers in affecting electrophoretic mobility has been examined. It has been observed that when freely absorbed, such polymers typically cause an increase, and not a decrease, in the electrophoretic mobility (see Brooks, *J. Colloid Interf. Sci.*, 1971 and Seaman, above). Various researchers have employed charged polymers in methods to obtain decreases in the mobility of macromolecules but not particles. Examples of these techniques are described in references such as Shimura et al., *Electrophoresis* 8:135-139 (1987) (charged polylysine added to ligand to aid biomolecule separation), and Vestermark, German Patent No. 2,040,091 (electrophoretic separation achieved through use of charged polyethylene glycol ions). These techniques do not aid in "masking" the native, i.e., effective surface charge of macromolecules, particles or cells, because the polymers in these cases are of opposite charge and will neutralize, not remove or mask, native charges on the macromolecules. What has not been previously recognized or accomplished, therefore, is the development of a system by which hydrophilic, uncharged polymers, such as polyethylene glycol (PEG), can be used to substantially reduce electrophoretic mobility by utilization of their polymer segment viscosity properties to alter the hydrodynamic nature of the "surface" of cells, particles and macromolecules in a concentration-dependent manner and/or in a manner based on their specific antigenic characteristics.

It is thus highly desirable to develop a system which will be able to employ polyethylene glycol or other hydrophilic neutral polymer in an affinity compound and which can retard electrophoretic mobility in a concentration-dependent manner so as to allow separation of a greater variety of cells, particles, macromolecules, or other substances.

SUMMARY OF THE INVENTION

According to the present invention, a method of reducing electrophoretic mobility of macromolecules, particles, cells and other substances in a controlled manner is provided which comprises interacting the macromolecules, particles or cells with a polymer-linked affinity compound comprised of a hydrophilic neutral polymer, such as polyethylene glycol, bound to a component comprising a hydrophobic compound, an immunocompound, such as an antibody or active antibody fragment or similar macromolecule with binding specificity (e.g., Protein A, Avidin, Protein G, Concanavalin A), or a ligand such as a hormone, drug, antigen, enzyme inhibitor or a hapten. The reduction in electrophoretic mobility achievable in the present invention is up to about 100% for particular substances, and the mobility reduction that is achieved is directly proportional to the concentration of the interacting affinity compound employed. The mobility reduction will also be a function of polymer molecular weight.

The present invention is particularly advantageous in that electrophoretic separation is now possible for a number of cells or particles whose normal surface charge structure would not allow separation under past systems. This is achieved with specificity as to particular cells or particles that can be separated, and the present invention allows for a controlled, concentration-dependent separation for a wide variety of substances.

DETAILED DESCRIPTION OF THE PREFERRED EMBODIMENTS

In the present invention, a hydrophilic neutral polymer such as polyethylene glycol is used in a two-component system to reduce electrophoretic mobility in a wide variety of macromolecules, particles and cells. The use of polyethylene glycol has been known in the separation of cells, such as described in Karr, Van Alstine et al, *J. Chromatography* 354: 269–282 (1986), in which it is employed in a phase partitioning system. However, phase partitioning, a liquid-liquid extraction technique which is relatively three-dimensional and energy independent, is quite unrelated to electrophoresis procedures, which are energy dependent and involve linear separation of materials based on differences in apparent surface charge. It has also been disclosed in a previous U.S. Pat. No. 4,690,749 (Van Alstine et al), to employ PEG in controlling electroosmosis. However,, in that patent, the PEG is permanently (i.e., covalently) linked to the surface of nonliving particles so as to produce test particles, e.g., glass beads, of defined mobility. In the present invention, the PEG-linked affinity compounds do not permanently bind to the particle or cell separated, and the technique disclosed herein can be used specifically for separating desired or target cells, after which the affinity ligand is released from and/or metabolized by those cells.

In the embodiments of the present invention, the polymer-linked affinity compound employed to reduce electrophoretic mobility in a controlled manner will be comprised primarily of a hydrophilic neutral polymer and a second component consisting of a hydrophobic compound, an immuno-compound, including antibodies, active antibody fragments or similar macromolecules with binding specificity (e.g., Protein A, Avidin, Protein G, Concanavalin A), or a ligand. For all of the embodiments, it is preferred that the hydrophilic neutral polymer neutral polymer employed comprise polyethylene glycol (PEG). However, other hydrophilic neutral polymers which can be covalently coupled to the second component of the polymer-linked affinity compound may be employed and may be advantageous under certain specific applications. Such advantages may include solubility, nonspecific interaction with substances of interest, chemical modification, FDA approval, secondary antigenicity, etc. Other neutral hydrophilic polymers suitable for use in the invention include polyvinyl alcohol, polyvinyl pyrrolidone, polypropylene glycol, polyethylene glycol-polypropylene glycol co-polymers, and polypropylene glycol-polyethylene glycol co-block polymers.

As discussed previously, it had been observed that free adsorption of neutral polymers typically increased the electrophoretic mobility of particles and cells. This is most likely due to the fact that the particles or cells non-specifically adsorb the polymers at multiple polymer contact points on their surface (see Brooks, above and Seaman, above). In the present invention, the hydrophilic neutral polymer-containing compounds adsorb at the "surface" of the macromolecule, cell or particle via demonstrably specific interactions. As a result, these adsorbate neutral affinity compounds alter particle or molecular electrohydrodynamic interaction with the suspending medium (increase local viscosity) at the particles or macromolecule's "surface", lowering cell/particle mobility. In the case of macromolecules, the affinity compounds of the present invention similarly contact the macromolecule at its outer periphery and alter its hydration, and the effect in reducing electrophoretic mobility is analogous to the effect of the compounds on the outer layers of cell or particle surfaces.

In one of the preferred embodiments of the invention, an immunocompound or fragment thereof, is employed as the second component of the polymer-linked affinity compound. By immunocompound is meant antibodies or fragments thereof, or similar compounds (such as Concanavalin A, Protein G, Protein A, Avidin) which can bind to specific "antigens". Particularly useful in the present invention are immunoglobulins (e.g., IgG) and their active fragments (e.g., F(ab) or Fc) derived therefrom. However, any antibody of human or animal derivation may be successfully employed in the invention. It has been shown by a group of authors including Karr, Harris, Van Alstine, et al., that PEG derivatized Protein A (which binds to antibody molecules) can be used to effect immunoaffinity partition. This technique may also work for immunoaffinity electrophoresis using PEG-Protein A or PEG-Protein G and unmodified antibodies or PEG-Avidin and Biotin-conjugated antibodies, etc. Affinity compounds containing an immunocompound as the second component are particularly advantageous in that they can be made very specific to the particular cell, particle, or macromolecule desired to be separated, and can then be used according to the method of the invention to successfully reduce mobility in a large number of substances having a surface or outer periphery charge structure which normally would not allow them to be separated by electrophoretic means. Immuno-affinity compounds can thus be modified in accordance with the method of the invention and rendered effective in reducing electrophoretic mobility of specific particles (e.g., cells such as subpopulations of lymphocytes) or any other molecules to which the antibodies or their active fragments are directed.

An additional feature of this aspect of the invention is the observation that the antibody/neutral polymer compounds greatly reduce the tendency to aggregate cells or particles, which would hinder specific cell separation, while at the same time providing concentration-dependent reduction in cell or particle electrophoretic mobility. The immuno-affinity compounds of the present invention are a great improvement over previous compounds as reported above which only achieved up to about 40% reduction in electrophoretic mobility. In the present invention, reduction in effective mobility of up to 100% can be achieved, in a manner dependent on the concentration (i.e., amount of bound antibody).

The preparation of hydrophilic neutral polymer-linked affinity compounds such as a PEG-antibody will preferably carried out by any of the many conventional processes generally known in the art. The covalent coupling of polyethylene glycol to an IgG antibody has been disclosed in Karr, Van Alstine et al., *J. Chromatography* 345:269-282 (1986), incorporated herein by reference. In this preferred preparation process, the polymer-linked affinity immunocompound of the present invention is prepared by mixing rabbit IgG directed against stroma from human red blood cells (RBC's), Fab fragments from the rabbit IgG, and an enriched IgG faction from sheep with cyanunic chloride-activated PEG 5000 or PEG 1900 monomethylether in a borate buffer. An approximately equimolar amount of activated PEG 5000 relative to IgG lysine amino grounds resulted in about 50% modification of the lysine amino groups. Unattached PEG was removed from the resulting mixture by diafiltration with 10 volumes of 0.05 M borate buffer and 0.025 M sodium acid. It will be well understood to those skilled in the art that many alternative methods of preparing the polymer-linked affinity compounds of the invention are known and can be employed, and particular methodology will depend upon the precise nature of the hydrophilic neutral polymer and the second component which are employed in the affinity compound.

In another embodiment of the present invention, the second component in the polymer-linked affinity compound comprises a hydrophobic compound. Hydrophobic compounds are well known in the art and their definition will be apparent to one skilled in this field. One preferred hydrophobic compound for use in the present invention comprises a fatty acid or alcohol alkyl derivative or acyl group with a hexadecane, octadecane, etc. tail including palmitic acid, stearic acid, oleic acid, etc. However, other hydrophobic compounds which can be covalently linked to the hydrophilic neutral polymer, such as 1-amino-octadecane may also be employed. Still other hydrophobic compounds contemplated as suitable for use in the present invention would include steroids, glycolipids, phospholipids, and other similar compounds. The specific hydrophobic compound used in any particular application will of course be dependent on the desired cell, particle or macromolecule to be separated.

The hydrophilic neutral polymer-hydrophobic affinity compounds employed in the present invention can be prepared by any suitable process conventionally known and used in the art. However, it is preferred that the hydrophobic compounds be linked to the hydrophilic neutral polymer by means of a covalent linkage, and it will be obvious to one skilled in the art that this can be carried out in a number of ways. It is preferred that a hydrophobic compound, such as a fatty acid or alcohol alkyl derivative, be combined with a PEG hydrophilic neutral polymer by suitable ether, amide, or ester linkage. In general, however, the hydrophobic compounds are most preferably linked to the hydrophilic neutral polymer by means of an ester linkage (such as those used in Example 2), but linkage through an ether, amine or other functional group is possible, and in certain cases may be beneficial. For example, ether linkages may confer longer shelf storage life. See, e.g., Harris, Van Alstine et al., *ACS Indus. Eng. Prod. R+D* 23:86-88 (1989).

The hydrophobic affinity compounds of the present invention show some specifity as to the cells and particles for which mobility is to be reduced, and these compounds have been shown by nonelectrophoretic methods to have differential interactions with specific cells such as normal and cancer cells, or different species of red blood cells. A particular advantage of the hydrophobic affinity compounds as used in the method of the invention is that the binding with the cells treated is readily reversible. This feature is highly advantageous where it is desired to separate cells, then remove the affinity compound so that the separated cells can be examined in native state. The compounds are not harmful to the electrophoretic apparatus used, and are typically employed and in such low concentrations that they can be easily and cheaply added to the buffer solutions normally used in existing electrophoretic techniques.

In still another aspect of the present invention, the second component of the polymer-linked affinity compound comprises a ligand. Ligands are well known as a chemical class, and their definition will be well known to one skilled in the art. Ligands useful in the present invention include a wide variety of small macromolecular substrates, such as hormones or antigens, or low molecular weight substances such as enzyme inhibitors and haptens. Still other ligands contemplated as suitable for use in the invention include neurotransmitters or mimetic drugs known to target specific cells, tissues or proteins. Examples of such substances include ouabain, nicotine, acetylcholine, etc.

As with the previously described embodiments, the affinity compounds of the present invention which include ligands are prepared in any of a number of conventional ways presently known in the art. One preferred method would comprise reacting an activated hydrophilic neutral polymer such as activated PEG 5000 or PEG 20000 with a ligand such as by the cyanuric chloride method described above. Such chemistry, directed at goals not overlapping the present patent application, are described in a variety of publications such as Karr, Van Alstine et al, *J. Chromatography* 345:269-282 (1986). However, it will be clear to one skilled in the art that a number of alternative preparation procedures can be employed, and the particular procedure chosen will depend on the particular hydrophilic neutral polymer and ligand used, and the target cell, macromolecule, or particle separated.

The present invention differs from the previous work of Müller et al, *Nucleic Acid Research* 9:95-115 (1981), in which dyes were covalently bound to a polyethylene glycol to specifically increase the frictional "surface" coefficient of DNA molecules gel electrophoresis, in that the Müller et al article did not disclose use of the dyes in binding cells or other particles. The ligand-affinity compounds of the present invention can be employed to reduce the non-gel based electrophoretic mobility of cells and particles in addition to macromolecules. Additionally, the ligand-affinity compounds of the present invention will be of varying reversibility, depending upon the particular ligand chosen, and reduce the mobility of cells and particles in a concentration-dependent manner. The ligand can be covalently or non-covalently bound to the hydrophilic neutral polymer as desired for a particular separation procedure.

In accordance with the present invention, electrophoretic separation can be accomplished in a variety of different manners. Depending on the affinity component utilized, separation can be achieved on the basis of specific/irreversible (e.g., PEG-derivatized antibody), specific/reversible (e.g., PEG-derivatized lectin), semi-specific, reversible (e.g., PEG-hydrophobic affinity ligand such as unsaturated PEG-fatty acid ester), relatively nonspecific reversible (e.g., saturated PEG-fatty acid ester or PEG-ionic interaction group (trimethylamine or sulphate)) or relatively nonspecific-irreversible (e.g., PEG-cyanuric chloride reacting with amino possessing particles or molecules) interactions.

In general, the affinity compounds appear to operate in reducing mobility of the macromolecules, cells, or particles treated by masking the "effective or apparent" surface charge. The neutral polymers apparently increase fluid viscous resistance to "surface" flow when anchored via the second component of the affinity compound to the particular cell, particle, or macromolecule separated. A general background as to the theory of electrophoresis and the effects of increasing local surface resistance to fluid flow can be found in Levine et al, *Biophys. J.* 42:127-135 (1983). In the present invention, the more neutral polymers which can be attached to the unit to be separated, the greater the effect in reducing mobility. Thus the reduction in electrophoretic mobility may be obtained in a manner directly proportional to the amount of affinity compound employed in the electrophoretic assay. The ability of the affinity compounds of the present invention to achieve concentration-dependent reduction in electrophoretic mobility has been confirmed in experimental tests. Their ability to specifically interact with a variety of biological and nonbiological substances (particularly cells) in a concentration dependent manner is documented. The polymer-linked affinity compounds of the invention can thus be used in a variety of applications when it is desired to achieve enhanced reduction of electrophoretic mobility in a controlled, concentration-dependent manner.

The present invention is advantageous in that the affinity compounds prepared as described above can be used in a wide variety of conventional electrophoretic apparatuses and methods in order to achieve separation for a great range of substances including cells, macromolecules and particles. By cells, it is generally meant the great diversity of biological or nonbiological cells, e.g., cancer cells, red blood cells, white blood cells, artificial cells, etc. which are often difficult to separate, but must be isolated for the great variety of research and diagnostic procedures performed using such materials. By macromolecules, it is generally contemplated that this will include many macromolecules known which are commonly isolated in research, most commonly those having molecular weights of generally anywhere from about 200 to 10,000,000 daltons. Included in this definition would be biological macromolecules such as DNA, proteins, protein active units, RNA, etc. By particles is meant any substance which does not fit any of the other classes above, but which has a definite mass and shape, and which can be isolated and separated by electrophoretic means. This will include bioparticles such as cell organelles, viruses, bacteria, yeasts, nuclei, nuclear fragments, membrane fragments, etc., and non-biological materials such as liposomes, polymer beads, micelles, and standard particles. Although particles of almost any size will be suitable for use in the present invention, the invention generally contemplates separating particles with sizes of from about 0.001 to 200 microns in diameter. It will be clear to one skilled in the art that the choice of which affinity compound to use will greatly depend on the substance to be separated, and whether other factors such as specificity or reversibility (as discussed above) are crucial.

In carrying out the method of the present invention, the polymer-linked affinity compounds described above are interacted with the target particle, cell, macromolecule, bioparticle or other substance in an electrophoretic system (such as gel electrophesis) in any of the many known conventional procedures commonly carried out in such a system. Generally, this will include a first step of introducing the desired polymer-linked affinity compound to a sample containing the particles or macromolecules to be separated which has been prepared for the appropriate electrophoresis apparatus chosen, followed by carrying out the particular electrophoretic technique chosen to best separate the target component. For example, in one preferred operation of the present invention, a polymer-linked affinity compound comprised of an antibody linked to polyethylene glycol (PEG) was used to specifically decrease the mobility of a sample of biological cells comprised of human erythrocytes. The PEG-Ab was added to the cells in a phosphate buffered saline solution, and the separation was carried out using a Rank Bros. cylindrical chamber cytropherometer set at 40 Volts DC. In experimental procedures conducted using this apparatus, it was observed that use of the affinity compounds of the method of the present invention decreased cell mobility in a concentration dependent manner.

The inventive method is not limited to any particular mode of operation, and it will be clear to one skilled in the art that the method of the present invention can be suitably carried out using a variety of conventional electrophoretic techniques and apparatuses. Included in such techniques would be systems employing equipment for carrying out capillary electrophoresis, gel electrophoresis, cylinder electrophoresis, continuous flow electrophoresis, slab gel electrophoresis, etc. The present invention will thus be applicable to a variety of conventional electrophoretic systems, and will be extremely advantageous in separating many substances which previously could not be separated in such systems.

The following examples are presented as illustrative only and are not intended to limit the scope of the invention in any way:

EXAMPLE I

Preparation of Polymer-Linked Affinity Compounds

The preparation of a PEG-antibody compound has been previous described in Karr, Van Alstine et al., *J. Chromatography* 345:269-282 (1986). In this example, a polyethylene glycol (PEG) was covalently coupled to IgG antibodies in the manner described below. Unless specified otherwise, all reagents used were ACS grade, or better quality, obtained from commercial sources. Distilled, filtered, 12 M$\Omega$/cm water was used throughout. The antibody used was Rabbit IgG directed against stroma from human RBCs (native antibody) which was obtained from Cooper Biomedical. Malvern, Pa., U.S.A. (lot 22196). Fab fragments derived from this same lot were prepared by controlled papain digestion by Jackson Immunoresearch, Avondale, Pa., U.S.A. An enriched IgG fraction from sheep, also directed against human RBCs, was provided by Dr. D. E. Brooks, University of British Columbia, Vancouver, Canada. This fraction, which had been derived from whole serum by ammonium sulfate precipitation, was then further purified by ion exchange chromatography using a DEAE-silica gel column. Both IgG samples agglutinated human RBCs at concentrations less than 0.2 $\mu$g/ml but did not agglutinate sheep RBCs.

In a typical preparation of the PEG-antibody compound, 12 mg of protein in 0.5 ml 0.05 M $Na_2B_4O_7$, pH 9.2, was added to 1.5 ml 0.1 M borate buffer. A volume of 1 ml of cyanuric chloride-activated PEG 5000 or PEG 1900 monomethyl ether in the borate buffer was then added at 4° C., and the mixture was stirred for hour. Unattached PEG was removed by diafiltration (50-ml Amicon cell, PM-30 membrane, 30,000 molecular weight cutoff) with 10 volumes of 0.05 M borate buffer and 0.025 M sodium azide to a final volume of 2 ml. Typically 27 mg of activated PEG 5000, approximately equimolar relative to IgG lysine amino groups (90 per molecule) resulted in about 50% modification of the lysine amino groups; only 70 of the 90 lysine groups were sensitive to our method of analysis (below). About half this amount of activated PEG (14 mg) gave 30% modification.

Analysis was performed by the Biuret and Habeeb methods (see Karr, Van Alstine, *J. Chrom.* 345:269-282). For the latter method (based on reaction of trinitrobenzenesulfonic acid with free lysine groups), we found it necessary to remove unattached PEG and to keep protein concentrations at approximately 0.6 mg/ml in order to obtain accurate and reproducible results. The 0.1 M borate buffer was used rather than 4% $NaHCO_3$ called for in the original procedure.

EXAMPLE II

Preparation of Other PEG-Linked Affinity Compounds

The preparation of other PEG-linked compounds has been described in Harris, Van Alstine et al, *J. Polymer Sci.* 22:341-352 (1984), incorporated herein by reference. This reference describes five general routes to synthesize PEG derivatives, and included preparation of the following PEG-linked compounds:

PEG-Aldehyde

This compound was prepared by three different routes. The first route, oxidation with pyridinium chlorochromate, is described in the Harris, Van Alstine et al. *J. Polymer Sci.* article, and the second and third routes proceeded as follows:

(i) From the diethyl acetal of $\alpha$-bromoacetaldehyde—Potassium tert-butoxide (1.0 g) was added to 5g PEG-3400 in 30 mL dry benzene or toluene and the mixture was stirred at room temperature for 30 min. $BrCH_2CH(OC_2H_5)_2$ (1.0 mL) was then added to dropwise and stirred continuously for 12 h. The reaction mixture was added to 200 mL dry ethyl ether and the resulting PEG-acetal filtered, placed in 20 mL 2 M HCl and stirred for 30 min. Absolute ethanol (50 mL) was added and the solution placed in a refrigerator at 0° C. for 2-3 h until the PEG-aldehyde had crystallized (add more ethanol if necessary). The crude, wet product was purified further by twice precipitating from 10-15 mL warm ethanol by addition to 100-150 mL dry ethyl ether. Yield: 4.5-5.0 g PEG-CHO, HPLC analysis revealed no chain cleavage. The percentage of aldehyde end groups was determined by Schiff test to be 65%.

(ii) By DMSO-acetic anhydride oxidation—PEG-3400 (5 g, 1.7 mmol) was added to 0.4 g acetic anhydride in 15 mL dimethylsulfoxide and stirred for 30 h at room temperature. At this point the reaction mixture was added dropwise to 100 mL dry ethyl ether, and reprecipitated two or three times from methylene chloride with ethyl ether. Yield was 4.5 g. The product retained a faint smell of dimethylsulfoxide. HPLC analysis showed no chain cleavage, and reduction with tritiated $NaBH_4$ indicated 80% aldehyde end groups. Reaction for longer periods, with excess anhydride, or at higher temperatures gave lower percentages of aldehyde end groups.

Of the three routes to the aldehyde, the DMSO-$Ac_2O$ approach seems to be the best in terms of ease of reaction and product purity.

PEG-Amine

Potassium hydroxide (0.02 g, 0.4 mmol) was added to ammonium chloride (0.36 g, 6.7 mmol) in 5 mL methanol. After the KOH pellets had dissolved, PEG-CHO (for 3000 g/mol, 2.0 g, 0.67 mmol) was added and the solution stirred for 15 min. A solution of $NaCHBH_3$ (0.42 g, 6.7 mmol) in 5 mL methanol was then added dropwise over 30 min., followed by addition of a second portion of KOH (0.1 g, 1.8 mmol). The solution was stirred for 24 h, and the product then precipitated by addition to ether. Recovery of the product was made difficult by its gummy nature which necessitated centrifugation rather than filtration. HPLC revealed no chain cleavage. A nitrous acid test was positive, and a Schiff test was negative. Chemical analysis is as follows:

Calcd C, 54.4; H, 9.09; N, 0.45. Found: C, 54.8; H, 9.94; N, 0.88.

We have found it difficult in general to obtain good elemental analyses on PEG derivatives because, we believe, of the tendency of these compounds to absorb protic solvents and salts.

PEG-Octadecyl Amine

The tosylate of PEG-3680 (monomethyl ether; 0.5 g, 0.14 mmol) and octadecyl amine (p.180 g, 0.67 mmol) were dissolved in benzene (10 mL) with a suspension of 0.2 g anhydrous sodium carbonate. This mixture was stirred at reflux for 60 h, and then the product precipitated by dropwise addition to 100 mL anhydrous ethyl ether. The reaction was monitored by inclusion of a small amount of $^{14}$C-labeled octadecyl amine (New England Nuclear). Yield was 0.42, g, 90% substitution.

PEG-Monopalmitate

PEG-6000 (Union Carbide; 20 g) was dissolved in 100 mL toluene, and 20 mL toluene were removed by distillation to remove water. Triethylamine (0.4 g; distilled over calcium hydride) was added to the PEG-toluene solution.

Palmitic acid (0.1 g; specific activity 5.9 mCi/mmol; Amersham) was dissolved in 2 ml 1.0 M NaOH in methanol to prepare the salt, and the solvent then removed by lyophilization. The lyophylate was dissolved in 10 mL anhydrous ethyl ether, to which was added dropwise 2 mL oxalyl chloride. The solvent was removed by rotary evaporation, and the residue resuspended in 10 mL toluene.

The PEG and acid chloride solutions were mixed and heated to reflux for 10 min. Cooling to 4° C. resulted in precipitation of the product. Yield was 19 g.

The product was purified in the three stages. In the first stage 12 g product was repeatedly (five times) dissolved in 200 mL acetone (slight warming aids solution) and precipitated by addition to 300 mL anhydrous ethyl ether at 0° C. TLC on silica gel (solvent D) cleanly separated PEG and PEG-ester ($R_f = 0.08$) from the fatty acid ($R_f = 0.85$), and revealed that the fatty acid contaminant had been reduced to 0.3% (w/w).

In the second stage the remaining fatty acid impurities were removed by chromatography on Sephadex LH-20 gel (Pharmacia) with 5:1 methanol: water eluent. This step reduced free fatty acid content to less than 0.1% (w/w) as shown by TLC. In a typical run, 10.5 g PEG/PEG-ester mixture were dissolved in 180 mL 5:1 methanol:water and loaded on the column at 120 mL/h and elution continued until 2.0 L solvent had passed through the column. The gel column was prepared from 350 g LH-20 and had final dimensions of $66 \times 20$ cm$^2$. Altering flow rate had little effect on separation efficiency, but increasing sample concentration (viscosity) dramatically reduced separation. Fractions were analyzed with Nessler's reagent, scintillation counting, and hydroxamic acid ester assay. Recovery was greater than 95% in all cases.

In the third stage the monoester (and any diester) were separated from unsubstituted PEG by chromatography on octylsepharose CL-4B (Pharmacia). In a typical run, 7 g PEG and PEG-ester in 5:1 methanol: water (from the LH-20 chromatography) were placed in a rotary evaporator and the methanol removed. The sample was then made up to 170 mL in water and applied to the column at a flow rate of 40 mL/h followed by water elution at 60 mL/h. The column distensions were $30 \times 5.3$ cm$^2$ (Pharmacia K26/40 column) with a 200 mL bed volume. Fractions were analyzed with Nessler's reagent for PEG. Approximately 100 mL water eluent were required for each gram of PEG to remove underivatized PEG from the column. After PEG could no longer be detected in the water eluent., 500 mL 5:1 methanol: water were applied to elute the ester. The compound was then isolated by rotary evaporation and freeze drying. Over 95% of the material applied to the column was recovered. The original mixture contained approximately one esterified PEG molecule in 60, while the final product contained 46 esterified molecules in 60. We have used the above procedure to prepare PEG-esters of the following fatty acids: 18:1; 12:0; 14:0; 16:0; 16:1; 18:0; 18:2; 18:3; and 20:4.

The PEG concentration of chromatography fractions was monitored by use of Nessler's reagent (Fisher). Sample (25 $\mu$L) was added to 5 mL Nessler's solution, mixed well, and allowed to settle for 2 min. The absorbance at 600 nm was read and compared with a standard curve. Because of nonlinearity of the Beer-Lambert plot, it was necessary to dilute samples to keep absorbance below 0.6 units.

The percentage of esterified PEG end groups was determined with the hydroxamic acid assay. The hydroxylamine reagent was prepared shortly before use by mixing equal volumes of 2 M HCl in propanol:water (4 vol/1 vol) was added to the tubes which were recapped and mixed. Then 100 $\mu$L of this sample were mixed with 400 $\mu$L alkaline hydroxylamine reagent.

After 20 to 25 min., 400 $\mu$L 2 MHCl in propanol:water (4 vol/1 vol) was added to the tubes which were recapped and mixed. Then 100 $\mu$l propanol, 100 $\mu$L methanol/water (5 vol/vol), and 200 $\mu$L 0.37 M FeCl$_3$ in 0.1 M HCl were added to each tube and the contents mixed. After 10 min the absorbance at 515 nm was measured and the result compared with a standard curve prepared from methyl esters of stearic, linolenic, or lauric acids (all standard curves were identical).

PEG-Octadecyl Ether

PEG-6000 (10 g; 0.0017 mol) was dissolved in 40 mL dry benzene and added dropwise to a suspension of potassium t-butoxide (10% excess; 0.4 g; 0.0037 mol) in 20 mL dry benzene under a nitrogen atmosphere. The mixture was allowed to stir at room temperature for 1 hour. Octadecyl bromide (two time excess; 2.2 g; 0.0067 mol) was dissolved in 15 mL dry benzene and added dropwise to the mixture, which was then stirred at room temperature for 72 h. After filtration to remove insoluble salts, the benzene was removed by rotoevaporation. The product was redissolved in methylene chloride and eluted down a short silica gel column (1 in. $\times 5$ in.) with methylene chloride. This removed dissolved salts and some of the unreacted PEG. The eluent was concentrated by rotoevaporation and the PEG-ether precipitated by dropwise addition to diethyl ether. Product isolated by precipitation was gummy and difficult to filter. The product was further purified by chromatography on Sephadex LH-20 gel with 5:1 methanol:water eluent (1 g dissolved in 30 mL eluent on a 1 in. $\times 12$ in. column with a flow rate of 0.5 mL/min). The eluent was concentrated by rotoevaporation and dried several hours in vacuo. Product thus isolated was 75-90% substituted with 0.2% (w/w) alkyl bromide contaminant remaining. Yield was 60%.

Alkyl bromide remaining was determined by GLC (30% SE-30). Substitution was determined by PNMR by determining the alkyl-H/ether-H ration, by HPLC (C18, 65:35 acetonitrile:methanol), and also by C-H elemental analysis.

EXAMPLE III

Interactions of Affinity Compounds In Electrophoretic Tests

Figure 1:
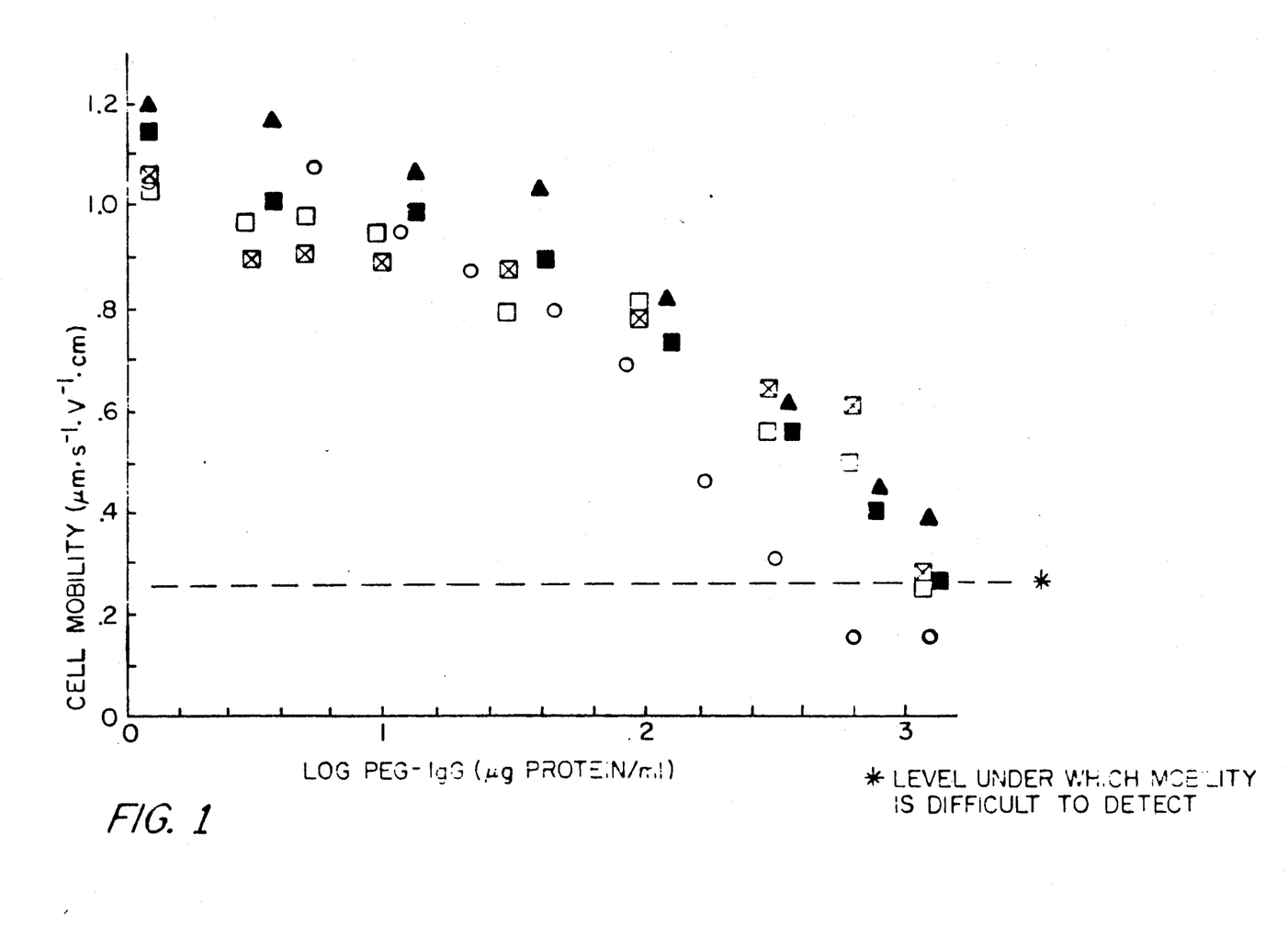
FIG. 1 is a graphic representation of the effects of immuno-affinity compounds of the present invention in reducing electrophoretic mobility of cells.

Electrophoretic mobility profiles of standard model cells (human erythrocytes) were obtained by interacting a PEG-antibody prepared in the manner of Example I with the cells in phosphate buffered saline in a Rank Bros. cylindrical chamber cytopherometer set at 40 V DC. Standard cell mobility is roughly 1.1 micrometer per second per volt per cm (i.e., velocity per field strength) expressed as $\mu m\ s^{-1}\ V^{-1}\ cm$. Five separate experiments with polyethylene glycol-immunoglobulin used to treat the cells were run, and the results are observed in the graph of FIG. 1. Each different immunoglobulin is represented by a different symbol. The standard error associated with each measurement (point) was ±10%, or less, of the mean. The results indicated that cell mobility was decreased for all PEG-immunoglobulin treated cells in a concentration dependent manner. The range of reduction ranged from roughly 1 $\mu g$ to 1 mg, and at the higher concentration levels of PEG-IgG, cell mobility effectively approached zero or a 100% reduction in mobility. It was also noted in these tests that cell aggregation normally associated with treatment by immunoglobulins alone was not observed with the PEG-immunoglobulin affinity compounds of the present invention.

EXAMPLE IV

Figure 2:
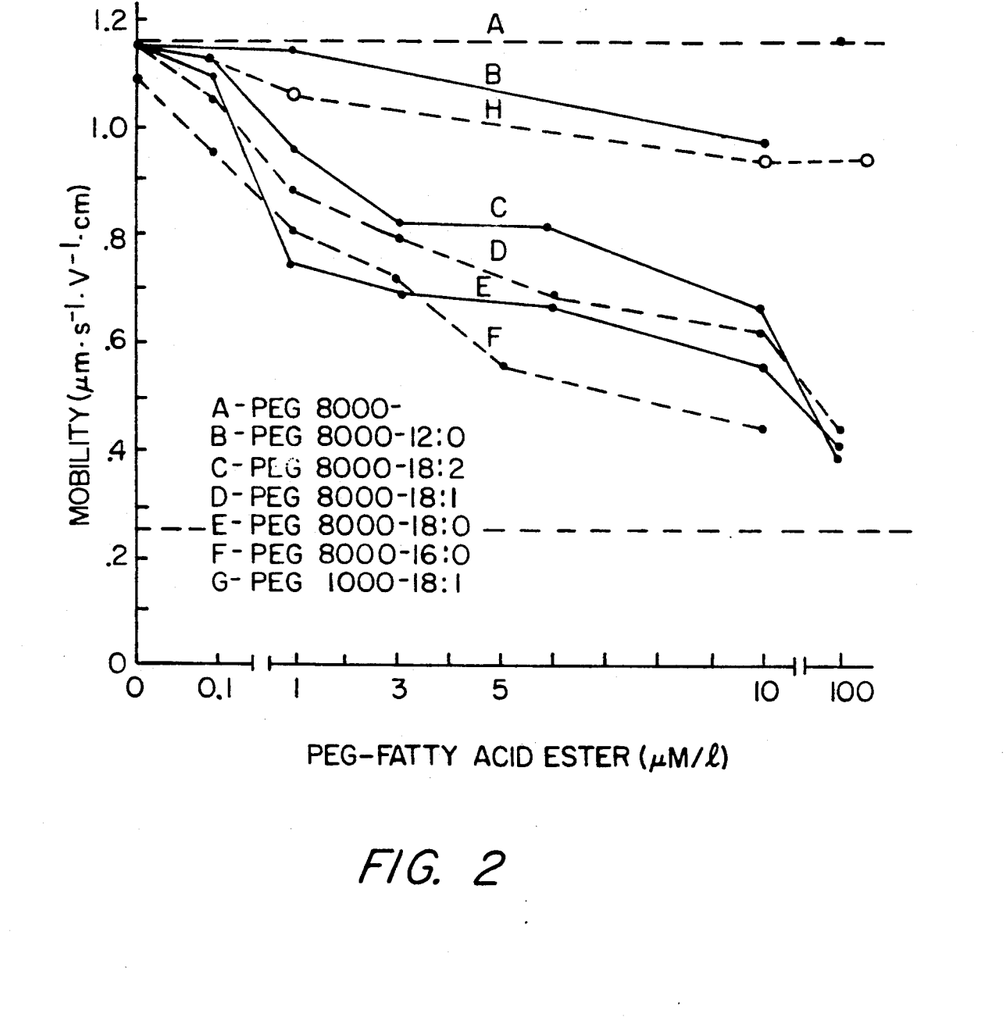
FIG. 2 is a graphic representation of the effects of various hydrophobic affinity compounds of the present invention in reducing electrophoretic mobility of cells.

The effect of a PEG-fatty acid ester affinity compound on cell mobility was tested in the same manner as described in Example III. The results of these tests can be observed in FIG. 2. Tests were made on PEG alone (as a control), and on PEG-fatty acid ester compounds varying in fatty acyl tail length and saturation. The PEG employed in most of these trials had a molecular weight of roughly 8000, and in one of the tests, a PEG of molecular weight of about 1000 was studied. The tests involved 3-5 trials for each of the affinity compounds as indicated in FIG. 2. Typical standard deviation for each point was ±10%, or less, of the mean. The results again indicated that the PEG-fatty acid ester affinity compounds were successful in producing a concentration-dependent reduction in electrophoretic mobility of the treated cells. It was also determined that the reduction in mobility was dependent upon the PEG head group molecular weight and the fatty acyl tail length and saturation. The particularly effective affinity compounds were those indicated at C-F in FIG. 2, wherein molecular weight of the PEG was around 8000, and the acyl tails of the compound had substantial tail length (hydrophobicity). The trials with lower molecular weight PEG and shorter tail length compounds both affected the mobility of the cells, but not as greatly as the effect observed with the compounds C-F.

The hydrophobic affinity compounds of the invention, although not as specific as the immuno-affinity compounds such as described in Example 4, are advantageous in that they can be produced at low cost, and are easily reversible with regard to the cells treated. Most cells have similar native electrophoretic mobilities due to the nature of the surface charges involved. The affinity compounds of the present invention will therefore allow for the controlled electrophoretic separation of cells and other particles in a manner heretofore unachievable, using equipment already owned by many laboratories.

EXAMPLE V

It is contemplated that a PEG-ligand affinity compound interaction will be carried out using the drug streptozotocin, which is specific for insulin-producing pancreatic Beta islet cells. Coupling PEG to streptozotocin may allow Beta cells to be separated electrophoretically from a mixture of cells from minced pancreatic islet tissue in that the Beta cells would be held back while the other cells (Delta, Alpha, fibroblasts, etc.) migrated at their normal mobility. In this interaction, coupling PEG to the streptozotocin will prevent it crossing the cell bilayer by diffusion (which can have harmful effects on cell viability). Separations based on other drugs/hormones coupled to PEG should also be readily possible, as one skilled in the art would be led to believe by the data embodied in the graphs of FIGS. 1 and 2.

What is claimed is:

1. A method of reducing electrophoretic mobility of macromolecules, particles cells or other substances in a controlled manner comprising interacting the substances with a polymer-linked affinity compound comprising a hydrophilic neutral polymer bound to a hydrophobic compound comprising a compound selected from the group consisting of a fatty acid or alcohol derivative, steroids, glycolipids, phospholipids and similar compounds so that a reduction of electrophoretic mobility of the treated substance is obtained that is directly proportional to the concentration of the polymer-linked affinity compound used in the interaction.

2. A method according to claim 1 wherein the hydrophilic neutral polymer comprises polyethylene glycol.

3. A method according to claim 1 wherein the hydrophilic neutral polymer is selected from the group consisting of polyvinyl alcohol, polyvinyl pyrollidone, polypropylene glycol, polyethylene glycol-polypropylene glycol co-polymers, and polypropylene glycol-polyethylene glycol co-block polymers.

4. A method according to claim 1 wherein the hydrophobic compound is bound to the hydrophilic neutral polymer by means of an ester linkage.

5. A method according to claim 1 wherein the hydrophobic compound is bound to the hydrophilic neutral polymer by means of an ether linkage.

6. A method according to claim 1 wherein the hydrophobic compound is bound to the hydrophilic neutral polymer by means of an amine linkage.

7. A method according to claim 1 wherein the hydrophobic compound is covalently bound to the hydrophilic neutral polymer.

8. A method of reducing electrophoretic mobility of macromolecules, particles, cells or other substances in a controlled manner comprising interacting the substances with a polymer-linked affinity compound comprised of a hydrophilic neutral polymer bound to a compound capable of binding to a specific antigen, said compound comprising a compound selected from the group consisting of an antibody, an immunoglobulin, an active antibody fragment, an active immunoglobulin fragment, Protein A, Protein G, avidin, concanavalin A, wheat germ lectin and other lectins capable of binding to a specific antigen, so that reduction of electrophoretic mobility of the treated substances is obtained that is directly proportional to the concentration of the polymer-linked affinity compound used in the interaction.

9. A method of reducing electrophoretic mobility of macromolecules, particles, cells or other substances in a controlled manner comprising interacting the substances with a polymer-linked affinity compound comprised of a hydrophilic neutral polymer non-covalently bound to a ligand so that a reduction of electrophoretic mobility of the treated substances is obtained that is directly proportional to the concentration of the polymer-linked affinity compound used in the interaction.

10. A method according to claim 9 wherein the ligand is selected from the group consisting of hormones, drugs, antigens, enzyme inhibitors haptens, neurotransmitters, ouabain, nicotine, acetylcholine, and other mimetic drugs.

* * * * *